(12) United States Patent
Tornier

(10) Patent No.: US 7,335,204 B2
(45) Date of Patent: Feb. 26, 2008

(54) OSTEOSYNTHESIS PLATE FOR THE UPPER END OF THE ARM BONE

(75) Inventor: Alain Tornier, Saint Ismier (FR)

(73) Assignee: Tornier SA, Saint Ismier (FR)

( * ) Notice: Subject to any disclaimer, the term of this patent is extended or adjusted under 35 U.S.C. 154(b) by 185 days.

(21) Appl. No.: 10/484,085

(22) PCT Filed: Jul. 17, 2002

(86) PCT No.: PCT/FR02/02545

§ 371 (c)(1),
(2), (4) Date: Jun. 4, 2004

(87) PCT Pub. No.: WO03/007832

PCT Pub. Date: Jan. 30, 2003

(65) Prior Publication Data

US 2004/0210220 A1    Oct. 21, 2004

(30) Foreign Application Priority Data

Jul. 17, 2001    (FR) .................................. 01 09507

(51) Int. Cl.
*A61B 17/56* (2006.01)
*A61F 2/30* (2006.01)
(52) U.S. Cl. ...................................... 606/69
(58) Field of Classification Search ................ 606/53, 606/60, 69, 70, 71–73
See application file for complete search history.

(56) References Cited

U.S. PATENT DOCUMENTS

| | | | |
|---|---|---|---|
| 4,867,144 A | 9/1989 | Karas et al. | |
| 4,903,691 A * | 2/1990 | Heinl | 606/70 |
| 5,171,289 A | 12/1992 | Tornier | |
| 5,314,485 A | 5/1994 | Judet | |
| 5,326,359 A | 7/1994 | Oudard | |
| 5,358,526 A | 10/1994 | Tornier | |
| 5,405,399 A | 4/1995 | Tornier | |
| 5,429,639 A | 7/1995 | Judet | |
| 5,458,650 A | 10/1995 | Carret et al. | |

(Continued)

FOREIGN PATENT DOCUMENTS

| | | |
|---|---|---|
| EP | 0 241 914 | 10/1987 |
| JP | 11299804 A * | 11/1999 |
| WO | WO 98 09578 | 3/1998 |

OTHER PUBLICATIONS

English Abstract for JP 11299804 A.*

(Continued)

*Primary Examiner*—Anuradha Ramana
(74) *Attorney, Agent, or Firm*—Faegre & Benson LLP

(57) ABSTRACT

An osteosynthesis plate designed for osteosynthesis of displaced fracture of the upper end of the arm bone includes a T-shaped main body (2) whereof the longitudinal branch (3) and the transverse branch (4) are respectively perforated with holes (5, 6, 8) for passing through screws for anchoring and fixing the plate against the outer profile of a bone, and fixing lugs (9) which extend from each side of the transverse branch (4) of the main body (2), the lugs being less thick than the main body and perforated with holes (10) which co-operate with other anchoring screws for completely fixing bone fragments when urged in contact with the bone external profile.

14 Claims, 3 Drawing Sheets

U.S. PATENT DOCUMENTS

| | | | |
|---|---|---|---|
| 5,505,731 A | 4/1996 | Tornier | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,718,705 A | 2/1998 | Sammarco | |
| 5,743,913 A | 4/1998 | Wellisz | |
| 5,749,872 A * | 5/1998 | Kyle et al. | 606/69 |
| 5,766,256 A | 6/1998 | Oudard et al. | |
| 5,824,106 A | 10/1998 | Fournol | |
| 5,879,395 A | 3/1999 | Tornier et al. | |
| 6,004,353 A * | 12/1999 | Masini | 623/22.21 |
| 6,096,040 A * | 8/2000 | Esser | 606/69 |
| 6,123,709 A * | 9/2000 | Jones | 606/69 |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,454,809 B1 | 9/2002 | Tornier | |
| 6,488,712 B1 | 12/2002 | Tornier et al. | |
| 6,506,191 B1 * | 1/2003 | Joos | 606/72 |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,969,406 B2 | 11/2005 | Tornier | |
| 7,033,396 B2 | 4/2006 | Tornier | |
| 2003/0009170 A1 | 1/2003 | Tornier | |
| 2003/0009171 A1 | 1/2003 | Tornier | |
| 2003/0028198 A1 | 2/2003 | Tornier et al. | |
| 2004/0134821 A1 | 7/2004 | Tornier | |
| 2004/0215200 A1 | 10/2004 | Tornier et al. | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2006/0015185 A1 | 1/2006 | Chambat et al. | |
| 2006/0173457 A1 | 8/2006 | Tornier | |
| 2006/0235538 A1 | 10/2006 | Rochetin et al. | |

OTHER PUBLICATIONS

Rochetin, U.S. Appl. No. 11/194,452, entitled "Patellar Retractor and Method of Surgical Procedure on Knee," filed Aug. 2, 2005.

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stern Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

* cited by examiner

OSTEOSYNTHESIS PLATE FOR THE UPPER END OF THE ARM BONE

BACKGROUND OF THE INVENTION

The present invention relates to an osteosynthesis plate designed to reunite splinters and fragmented bodies of bone belonging to a humerus or to any other long bone.

Patent EP241914 discloses plates of this kind which have a T shape whose transverse branch and longitudinal branch are perforated with holes of oval conical profile. On one of the faces of each branch, the plate comprises grooves into which the holes provided for the passage of fixation screws open.

The plate is thus used with bone screws comprising a double thread, on the one hand for fixation in the bone and on the other hand for receiving said plate by placement of a nut, in order to obtain a device permitting stabilization by tightening.

The plate permits reduction of fractures of the anatomical neck of the humerus, of the ends of the humerus situated at the elbow, of the upper ends of the tibia, and of other lesions in proximity to the bases.

SUMMARY OF THE INVENTION

The osteosynthesis plate according to the present invention is aimed at refining the T-shaped plates in order to improve their fixation in the bone and more particularly the retention and fixation of the tuberosities, for example in the area of the upper end of a humerus.

The osteosynthesis plate according to the present invention is designed for osteosynthesis of displaced fractures of the upper end of the humerus and comprises a T-shaped main body whose longitudinal branch and transverse branch are respectively perforated with holes for the passage of screws for anchoring and fixing said plate against the outer profile of a bone, and fixation tabs which extend from each side of the transverse branch of the main body, said tabs being less thick than the main body and being perforated with holes which cooperate with other anchoring screws to complete the fixation of bone fragments in contact with the outer profile of the bone.

The osteosynthesis plate according to the present invention comprises a transverse branch provided with at least one fixation tab oriented in a direction substantially perpendicular to the longitudinal branch, at least one tab oriented in a direction parallel to the longitudinal branch, and at least one tab which is inclined and situated between the first two.

The osteosynthesis plate according to the present invention comprises fixation tabs which are of small size and of low thickness compared to the size and thickness of the longitudinal branch and of the transverse branch so as to be modeled to the outer profile of the bone and perfectly follow the contours of the latter by bearing against it.

The osteosynthesis plate according to the present invention comprises a main body which has a curved tile shape with radius R1, the concavity of which is directed toward the bone, in order to optimally adapt to the bone profile in the transverse plane.

The osteosynthesis plate according to the present invention comprises a curvature with radius R situated in the region joining the longitudinal branch and the transverse branch, and of which the convexity is directed toward the bone, in such a way as to adapt to the bone profile in the region of application of the plate.

BRIEF DESCRIPTION OF THE DRAWINGS

The following description in which reference is made to the attached drawings, which are given as nonlimiting examples, will permit a better understanding of the invention, of its characteristics, and of the advantages it is likely to afford.

DETAILED DESCRIPTION OF THE PREFERRED EMBODIMENTS

Figure 1:
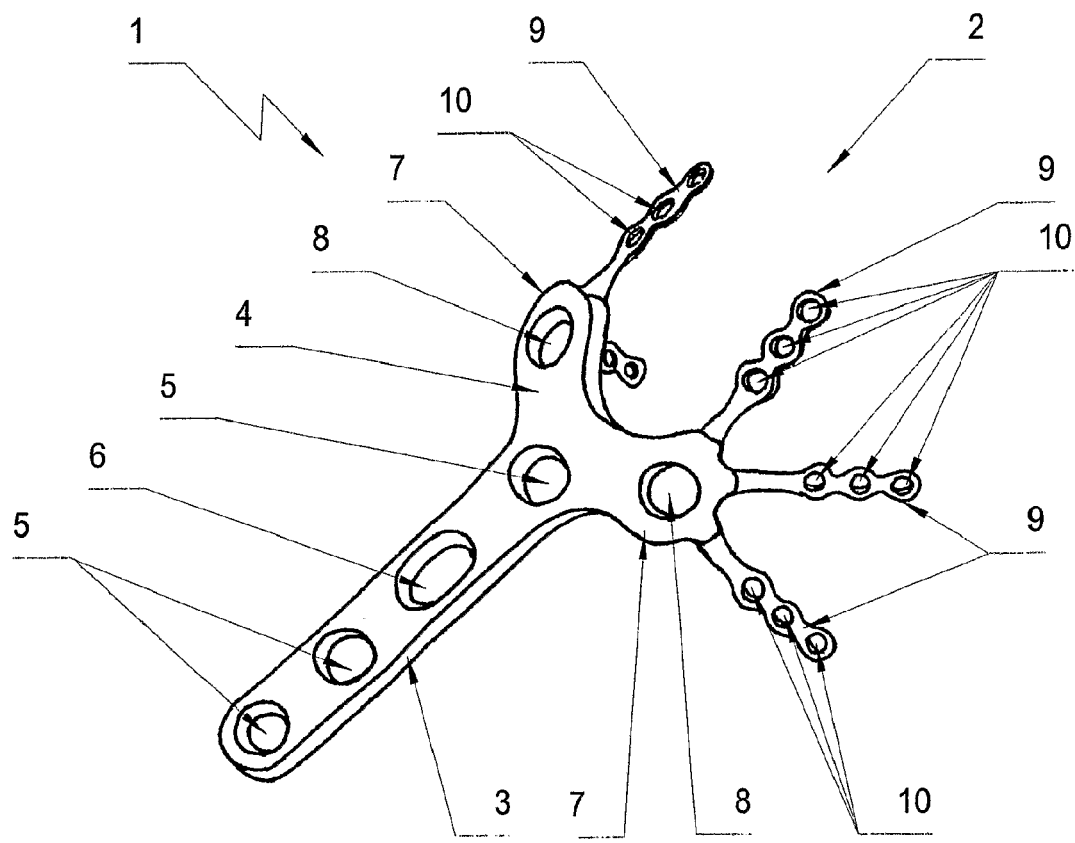
FIG. 1 is a perspective view illustrating the osteosynthesis plate according to the present invention.

In FIG. 1, an osteosynthesis plate 1 is shown which comprises a T-shaped main body 2 delimiting a longitudinal branch 3 and a transverse branch 4.

The longitudinal branch 3 forming the splint part of the osteosynthesis plate 1 is perforated with open holes 5, between which at least one hole 6 of oblong profile is provided.

The transverse branch 4 forming the head part of the osteosynthesis plate 1 has a slightly curved outer profile in order to delimit, on either side of the longitudinal branch 3, a rounded portion 7 perforated with a hole 8.

The transverse branch 4 is continued, in the area of its rounded portions 7, by a series of fixation tabs 9 which are of less thickness than that of the body 2 and which are perforated with holes 10.

The fixation tabs 9 extend from the peripheral edge of the main body 2 of the osteosynthesis plate 1.

Each rounded portion 7 of the transverse branch 4 comprises at lest one tab 9 oriented in a direction substantially perpendicular to the longitudinal branch 3, at least one tab 9 oriented in a direction parallel to the longitudinal branch 3, and at least one tab 9 which is inclined and situated between the first two.

The holes 10 formed in the tabs 9 are of small dimension in order to receive anchoring screws which are different than those cooperating with the holes 5, 6 of the longitudinal branch 3 and of the transverse branch 4.

The tabs 9 are of small size and of less thickness compared to the size and thickness of the longitudinal branch 3 and of the transverse branch 4 of the plate 1, in order to be modeled to the outer profile of the bone and perfectly follow the contours of the latter by bearing against it.

Figure 2:
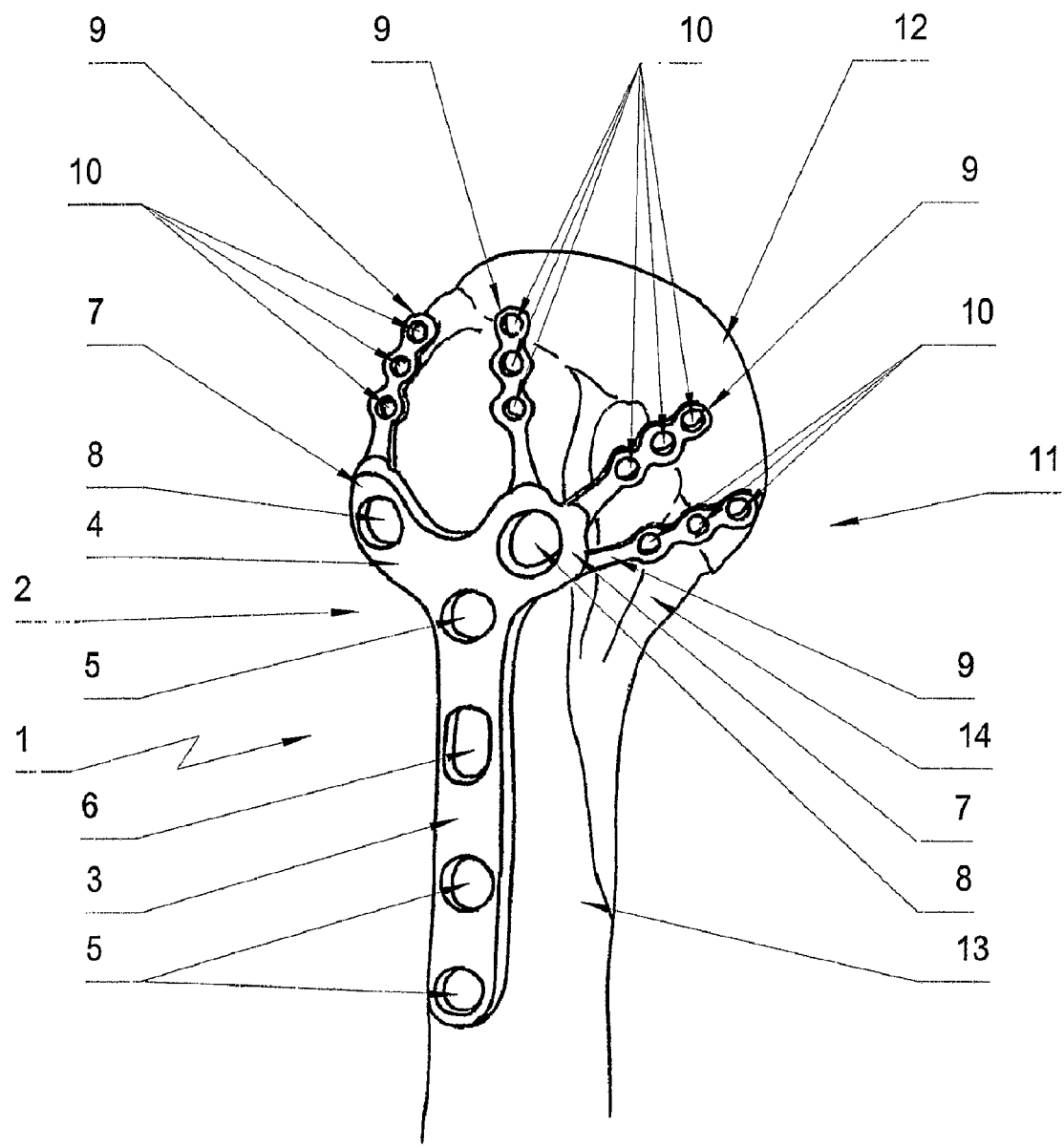
FIG. 2 is a view showing the placement of the osteosynthesis plate according to the invention on a bone.

In FIG. 2, the osteosynthesis plate 1 has been shown bearing, for example, against the upper end of a humerus 11.

After anchoring of the bone screws of the splint against the humeral diaphysis 13, the placement of the osteosynthesis plate 1 allows the head 12 of the humerus to be brought back into contact with the aid of the screws positioned in the two holes 8 of the transverse branch 4 and the upper hole 5 of the longitudinal branch 3.

After anchoring of the bone screws, the placement of the osteosynthesis plate 1 also permits retention and fixation of the tuberosities against the epiphysis of the humerus 11.

It will be noted that the longitudinal branch 3 of the osteosynthesis plate 1 is fixed against the diaphyseal part 13 of the humerus 11, while the transverse branch 4 is fixed against the epiphyseal part 14 of the humerus 11, so that the tabs 9 are modeled about the outer profile of the tuberosities of the humerus before these are fixed, by anchoring screws passing through the holes 10.

It will be noted that the direction of the upper hole 5 of the longitudinal branch 3 and of the holes 8 of the transverse branch 4 is such that it allows positioning of the screws in a region near the center of the head 12 of the humerus.

The fact that the osteosynthesis plate 1 comprises fixation tabs 9 for the tuberosities in the area of the transverse branch 4 means that the muscle stresses applied to the tuberosities can be transmitted directly to the T-shaped main body 2 constituting said plate.

Likewise, the arrangement of the tabs 9 relative to one another makes it possible to constitute a kind of basket which envelops and maintains the tuberosities.

Figure 3:
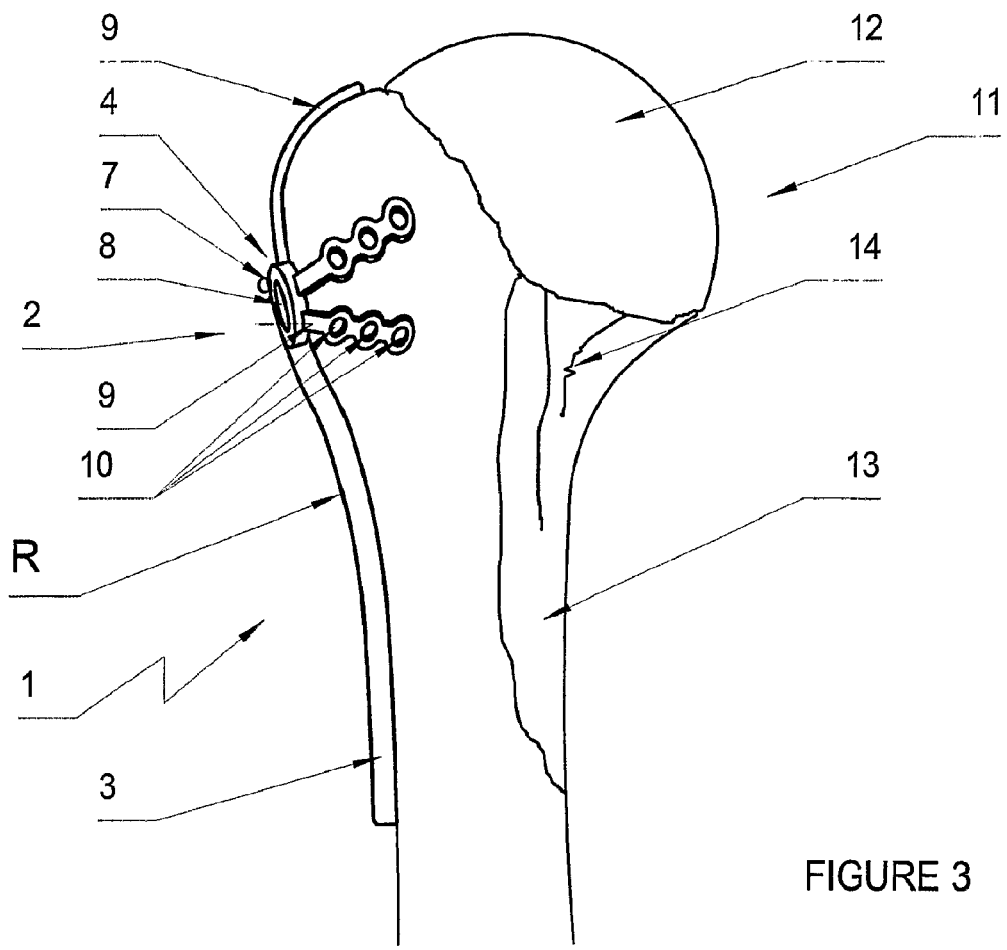
FIG. 3 is a front view showing the placement of the osteosynthesis plate according to the invention on a bone.

FIG. 3 is a front view of the plate 1 which has a curved form with radius R situated below the region joining the longitudinal branch 3 and the transverse branch 4, the convexity of which is directed toward the humerus, in such a way as to adapt to the lateral bone profile in the frontal plane.

Figure 4:
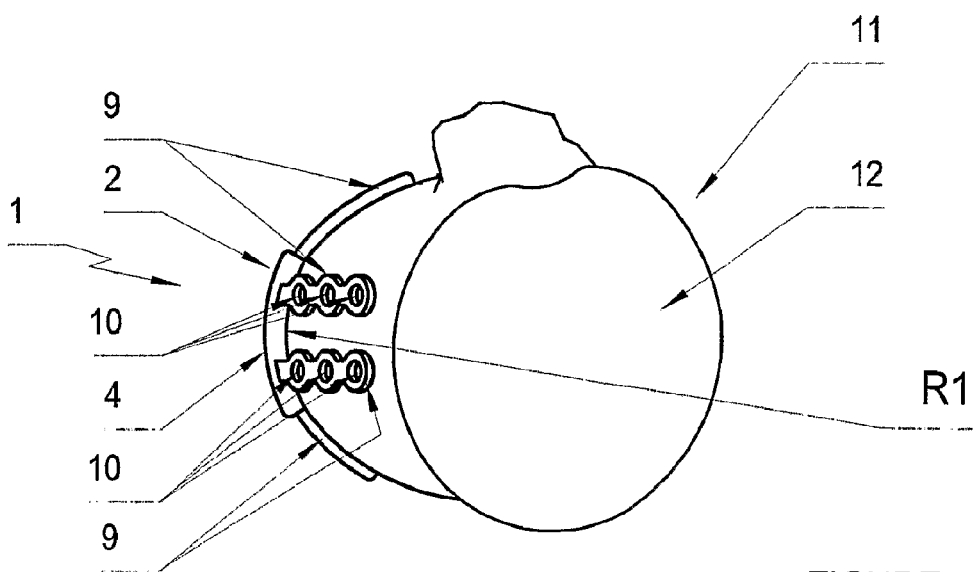
FIG. 4 is a plan view showing the placement of the osteosynthesis plate according to the invention on a bone.

FIG. 4 is a plan view of the plate 1 as a whole showing that the body 2 has a curved tile shape with radius R1, the concavity of which is directed toward the humerus, in order to adapt optimally to the bone profile in the transverse plane.

It will be noted that the main body 2 of the osteosynthesis plate 1 can have different outer shapes without this changing the subject of the present invention, which consists in arranging fixation tabs 9 around the body 2.

It must also be appreciated that the above description has been given only by way of example and that it does not in any way limit the field of the invention, and that replacing the design details which have been described with any other equivalents would not constitute a departure therefrom.

The invention claimed is:

1. An osteosynthesis plate designed for osteosynthesis of displaced fractures of the upper end of the humerus, comprising:
   a T-shaped main body having a longitudinal branch and a transverse branch that are respectively perforated with holes for the passage of screws for anchoring and fixing the plate against an outer profile of a bone; and
   fixation tabs which extend from each side of the transverse branch of the main body wherein the tabs are of small size and of low thickness compared to the size and thickness of the longitudinal branch and the size and thickness of the transverse branch so as to be modeled to an outer profile of a bone and follow the contours of a bone by bearing against a bone, and being perforated with holes which cooperate with other anchoring screws to complete the fixation of bone fragments in contact with an outer profile of a bone.

2. The osteosynthesis plate as claimed in claim 1, wherein the transverse branch comprises at least one tab oriented in a direction substantially perpendicular to the longitudinal branch, at least one tab oriented in a direction parallel to the longitudinal branch, and at least one tab which is inclined and situated between the first two tabs.

3. The osteosynthesis plate as claimed in claim 1, wherein the main body has a curved shape with radius R1, the concavity of which is directed toward a bone, in order to optimally adapt to a bone profile in a transverse plane.

4. The osteosynthesis plate as claimed in claim 1, wherein the plate has a curvature with radius R situated in the region joining the longitudinal branch and the transverse branch and of which the convexity is directed toward a bone, in such a way as to adapt to a bone profile in the region of application of the plate.

5. An osteosynthesis plate designed for osteosynthesis of displaced fractures of an upper end of a humerus, comprising:
   a T-shaped main body having a longitudinal branch and a transverse branch that are respectively perforated with holes for cooperating with anchoring screws for anchoring and fixing the plate against an outer profile of a bone; and
   fixation tabs extending from a peripheral edge of each side of the transverse branch, wherein the tabs are smaller and thinner than the main body and being perforated with holes of small dimension that cooperate with different anchoring screws than the anchoring screws cooperating with the holes of the longitudinal and transverse branches to fix bone fragments in contact with an outer profile of a bone.

6. The osteosynthesis plate as claimed in claim 5, wherein each side of the transverse branch comprises at least one tab oriented in a direction substantially perpendicular to the longitudinal branch, at least one tab oriented in a direction parallel to the longitudinal branch, and at least one tab which is inclined and situated between the first two tabs.

7. The osteosynthesis plate as claimed in claim 5, wherein the tabs are structured and arranged so as to be modelable to an outer profile of a bone and follow contours of a bone by bearing against a bone.

8. The osteosynthesis plate as claimed in claim 5, wherein the main body has a curved shape with radius R1, a concavity of which is directed toward a bone, in order to adapt to a bone profile in a transverse plane.

9. The osteosynthesis plate as claimed in claim 5, having a curvature with radius R situated in a region joining the longitudinal branch and the transverse branch, and a convexity of which is directed toward a bone to adapt to a bone profile in a region of application of the plate.

10. An osteosynthesis plate designed for osteosynthesis of displaced fractures of an upper end of a humerus, comprising:
    a T-shaped main body having a longitudinal branch and a transverse branch that are respectively perforated with holes for cooperating with anchoring screws for anchoring and fixing the plate against an outer profile of a bone, wherein the distal ends of the transverse branch are rounded; and
    fixation tabs extending from a peripheral edge of each of the rounded distal ends of the transverse branch, the tabs being thinner and less wide than the longitudinal and transverse branches of the main body and being perforated with holes of small dimension to receive anchoring screws different than anchoring screws cooperating with the holes of the longitudinal and transverse branches to fix bone fragments in contact with an outer profile of a bone.

11. The osteosynthesis plate as claimed in claim 10, wherein each side of the transverse branch comprises at least one tab oriented in a direction substantially perpendicular to the longitudinal branch, at least one tab oriented in a direction parallel to the longitudinal branch, and at least one tab which is inclined and situated between the first two tabs.

12. The osteosynthesis plate as claimed in claim 10, wherein the fixation tabs are structured and arranged so as to be modelable to an outer profile of a bone and follow contours of a bone by bearing against a bone.

13. The osteosynthesis plate as claimed in claim 10, wherein the main body has a curved shape with radius R1, a concavity of which is directed toward a bone, in order to adapt to a bone profile in a transverse plane.

14. The osteosynthesis plate as claimed in claim 10, having a curvature with radius R situated in a region joining the longitudinal branch and the transverse branch, and a convexity of which is directed toward a bone to adapt to a bone profile in a region of application of the plate.

* * * * *